(12) United States Patent
Khanmamedova et al.

(10) Patent No.: US 9,233,884 B2
(45) Date of Patent: Jan. 12, 2016

(54) CATALYST FOR CONVERSION OF HYDROCARBONS, PROCESS OF MAKING AND PROCESS OF USING THEREOF—BIMETALLIC DEPOSITION

(75) Inventors: Alla K. Khanmamedova, Sugar Land, TX (US); Scott F. Mitchell, The Woodlands, TX (US); Scott A. Stevenson, Houston, TX (US); Gopalakrishnan G. Juttu, Glen Mills, PA (US)

(73) Assignee: SAUDI BASIC INDUSTRIES CORPORATION, Riyadh (SA)

(*) Notice: Subject to any disclaimer, the term of this patent is extended or adjusted under 35 U.S.C. 154(b) by 1975 days.

(21) Appl. No.: 12/125,184

(22) Filed: May 22, 2008

(65) Prior Publication Data

US 2008/0293987 A1 Nov. 27, 2008

Related U.S. Application Data

(60) Provisional application No. 60/931,610, filed on May 24, 2007.

(51) Int. Cl.
| | |
|---|---|
| C07C 1/20 | (2006.01) |
| B01J 29/04 | (2006.01) |
| B01J 29/40 | (2006.01) |
| B01J 29/44 | (2006.01) |
| C07C 2/24 | (2006.01) |
| C07C 2/66 | (2006.01) |
| C07C 2/76 | (2006.01) |
| C07C 6/12 | (2006.01) |
| C10G 35/095 | (2006.01) |

(52) U.S. Cl.
CPC .......... *C07C 1/20* (2013.01); *B01J 29/047* (2013.01); *B01J 29/405* (2013.01); *B01J 29/44* (2013.01); *C07C 2/24* (2013.01); *C07C 2/66* (2013.01); *C07C 2/76* (2013.01); *C07C 6/123* (2013.01); *C07C 6/126* (2013.01); *C10G 35/095* (2013.01); *B01J 2229/186* (2013.01); *C07C 2529/44* (2013.01); *C10G 2300/1081* (2013.01); *C10G 2300/1088* (2013.01)

(58) Field of Classification Search
None
See application file for complete search history.

(56) References Cited

U.S. PATENT DOCUMENTS

| | | | |
|---|---|---|---|
| 3,216,789 A | 11/1965 | Breck et al. | |
| 3,926,782 A | 12/1975 | Plank et al. | |
| 4,310,440 A | 1/1982 | Wilson et al. | |
| 4,440,871 A | 4/1984 | Lok et al. | |
| 4,645,586 A | 2/1987 | Buss | |
| 4,652,689 A | 3/1987 | Lambert et al. | |
| 4,830,732 A | 5/1989 | Mohr et al. | |
| 4,837,397 A | 6/1989 | Absil et al. | |
| 4,867,864 A | 9/1989 | Dessau | |
| 4,892,646 A | 1/1990 | Venkat et al. | |
| 4,908,341 A | 3/1990 | Pruden et al. | |
| 4,954,245 A | 9/1990 | Miller et al. | |
| 4,962,250 A | 10/1990 | Dessau et al. | |
| 5,028,312 A | 7/1991 | Miller et al. | |
| 5,185,484 A | 2/1993 | Del Rossi et al. | |
| 5,209,918 A | 5/1993 | Hellring et al. | |
| 5,210,364 A | 5/1993 | Barri et al. | |
| 5,215,950 A | 6/1993 | Bournonville et al. | |
| 5,227,557 A * | 7/1993 | Bournonville et al. | ....... 585/419 |
| 5,246,688 A | 9/1993 | Faust et al. | |
| 5,268,161 A | 12/1993 | Nakagawa | |
| 5,456,822 A * | 10/1995 | Marcilly et al. | .............. 208/136 |
| 5,510,016 A | 4/1996 | Hilbert et al. | |
| 5,518,707 A | 5/1996 | Bedard et al. | |
| 5,633,422 A | 5/1997 | Murray | |
| 5,667,695 A | 9/1997 | Bedard et al. | |
| 5,773,381 A | 6/1998 | Verduijn et al. | |
| 5,885,443 A | 3/1999 | Bogdan et al. | |
| 5,935,415 A | 8/1999 | Haizmann et al. | |
| 5,977,009 A | 11/1999 | Faraj | |
| 5,993,642 A | 11/1999 | Mohr et al. | |
| 6,046,373 A | 4/2000 | Sun | |
| 6,048,449 A | 4/2000 | Bogdan et al. | |

(Continued)

FOREIGN PATENT DOCUMENTS

| | | |
|---|---|---|
| WO | 2005003031 A1 | 1/2005 |
| WO | 2006071873 A1 | 7/2006 |

OTHER PUBLICATIONS

Bebon et al., "Synthesis of zeolites: study and application of a new process of homogeneous shaking out of the medium to minimize the shear rate during the crystallization", Microporous and Mesoporous Materials, 53 (2002), pp. 13-20.

(Continued)

*Primary Examiner* — Tam M Nguyen
(74) *Attorney, Agent, or Firm* — Cantor Colburn LLP

(57) ABSTRACT

This invention is for a catalyst for conversion of hydrocarbons. The catalyst is a germanium zeolite, such as Ge-ZSM-5, on which at least two metals, platinum and at least one other metal selected from Group 7, Group 8, Group 9, Group 10 and tin, are deposited on the germanium zeolite. Examples of the other metal are iridium, rhenium, palladium, ruthenium, rhodium, iron, cobalt and tin. The catalyst is prepared by synthesizing a germanium zeolite; depositing platinum and at least one other metal on the germanium zeolite; and calcining after preparation of the zeolite, before depositing the metals or after depositing the metals. The catalyst may be used in a process for the conversion of hydrocarbons, such as propane to aromatics, by contacting the catalyst with a hydrocarbon stream containing alkanes, olefins and mixtures thereof having 2 to 12 carbon atoms per molecule and recovering the product.

14 Claims, 14 Drawing Sheets

(56) References Cited

U.S. PATENT DOCUMENTS

| | | |
|---|---|---|
| 6,083,379 A | 7/2000 | Drake et al. |
| 6,160,191 A | 12/2000 | Smith et al. |
| 6,177,374 B1 | 1/2001 | Pradhan et al. |
| 6,245,219 B1 | 6/2001 | Kao |
| 6,410,473 B1 | 6/2002 | Pinnavaia et al. |
| 6,486,373 B1 | 11/2002 | Abichandani et al. |
| 6,740,228 B1 | 5/2004 | Verduijn et al. |
| 6,784,333 B2 | 8/2004 | Juttu et al. |
| 6,884,531 B2 | 4/2005 | Dabbousi et al. |
| 6,914,165 B2 | 7/2005 | Flego et al. |
| 7,029,572 B2 | 4/2006 | Maesen et al. |
| 7,037,422 B2 | 5/2006 | Maesen et al. |
| 7,037,871 B1 | 5/2006 | Galperin et al. |
| 7,307,422 B2 | 12/2007 | Van Helvoort et al. |
| 7,414,007 B2 | 8/2008 | Gillespie et al. |
| 2001/0024635 A1 | 9/2001 | Beck et al. |
| 2003/0073856 A1 | 4/2003 | Hancu et al. |
| 2003/0121827 A1 | 7/2003 | van den Berge et al. |
| 2004/0028584 A1 | 2/2004 | Juttu et al. |
| 2004/0121902 A1 | 6/2004 | Chang et al. |
| 2004/0192539 A1* | 9/2004 | Juttu et al. ............ 502/60 |
| 2004/0200757 A9 | 10/2004 | Takewaki et al. |
| 2005/0143610 A1 | 6/2005 | Mitchell et al. |
| 2005/0158238 A1 | 7/2005 | Tatsumi et al. |
| 2005/0197515 A1 | 9/2005 | Juttu et al. |
| 2005/0209093 A1 | 9/2005 | Chester et al. |
| 2005/0271582 A1 | 12/2005 | Barea et al. |
| 2005/0274647 A1 | 12/2005 | Boehmer et al. |
| 2006/0115415 A1 | 6/2006 | Yuen |
| 2006/0140854 A1 | 6/2006 | Juttu et al. |
| 2006/0205990 A1 | 9/2006 | Rice |
| 2008/0154079 A1 | 6/2008 | Ellis et al. |
| 2008/0255398 A1 | 10/2008 | Stevenson et al. |
| 2008/0293988 A1 | 11/2008 | Mitchell et al. |
| 2008/0293989 A1 | 11/2008 | Khanmamedova et al. |
| 2008/0293990 A1 | 11/2008 | Stevenson et al. |
| 2012/0122662 A1 | 5/2012 | Khanmamedova et al. |
| 2013/0324778 A1 | 12/2013 | Mitchell et al. |

OTHER PUBLICATIONS

International Search Report; International Application No. PCT/US08/06632; International Filing Date May 23, 2008; Date of Mailing Aug. 15, 2008; 3 pages.

Written Opinion of the International Searching Authority; International Application No. PCT/US08/06632; International Filing Date May 23, 2008; Date of Mailing Aug. 15, 2008, 4 pages.

Aboul-Gheit et al.; "Catalytic para-xylene maximization: III. Hydroisomerization of meta-xylene on H-ZSM-5 catalysts containing different platinum contents"; J. Chem. Technol Biotechnol; 1999; 74; pp. 771-777.

Halgeri; "Disproportionation of Toluene Over a Metal-supported Type L-Zeolite Catalyst"; J. Chem. Tech. Biotechnol.; 1981;31; pp. 541-545.

International Preliminary Report on Patentability; Application No. PCT/US2010/058723; Date of Mailing: Jun. 14, 2012; 7 Pages.

International Search Report; International Application No. PCT/US2010/058723; International Filing Date: Dec. 2, 2010; Date of Mailing: Feb. 10, 2011; 3 Pages.

Kosslick et al.; "Synthesis and Characterization of Ge-ZSM-5 Zeolites"; J. Phys. Chem.; vol. 97; 1993; pp. 5678-5684.

NAPTHA; Safety Data Sheet; Tesoro; 12 Pages.

Olson et al.; "Chemical and Physical Properties of the ZSM-5 Substitutional Series"; Journal of Catalysis 61; pp. 390-396; 1980.

Pellet; "Hydrogen Transfer Catalysis by Platinum on Zeolites"; J. of Catalysis 177; pp. 40-52; 1998.

Van De Water et al.; "Improved Catalytic Activity Upon Ge Incorporation into ZSM-5 Zeilites"; Journal of Catalysis; vol. 223; 2004; pp. 170-178.

Written Opinion of the International Searching Authority; International Application No. PCT/US2010/058723; International Filing Date: Dec. 2, 2010; Date of Mailing: Feb. 10, 2011; 5 Pages.

* cited by examiner

CATALYST FOR CONVERSION OF HYDROCARBONS, PROCESS OF MAKING AND PROCESS OF USING THEREOF—BIMETALLIC DEPOSITION

BACKGROUND OF THE INVENTION

1. Field of the Invention

This invention relates to a catalyst for hydrocarbon conversion, e.g., a catalyst for the aromatization of alkanes, olefins and mixtures thereof having two to twelve carbon atoms per molecule. The catalyst is a microporous silicate, aluminosilicate, aluminophosphate or silicoaluminophosphate on which a metal has been deposited.

2. Description of the Prior Art

Crystalline silicates, aluminosilicates, aluminophosphates and silicoaluminophosphates are known catalysts for hydrocarbon conversion and may contain other metals. An aluminosilicate such as a zeolite may include not only aluminum and silicon but other trivalent elements which replace aluminum and other tetravalent elements which replace silicon. Also, other elements may be deposited on the silicate, aluminosilicate, aluminophosphate or silicoaluminophosphate.

U.S. Pat. No. 4,310,440 discloses crystalline aluminophosphates having a framework structure with chemical composition in mole ratios of $1Al_2O_3:1.0\pm0.2P_2O_5$ and being microporous with uniform pores of nominal diameters from about 3 to about 10 angstroms.

U.S. Pat. No. 4,440,871 discloses crystalline microporous silicoaluminophosphates having pores which are uniform and have nominal diameters of greater than about 3 angstroms with a chemical composition of mole fractions of silicon, aluminum and phosphorus within the pentagonal composition area defined by

|   | Mole Fraction | | |
|---|---|---|---|
|   | x | y | z |
| A | 0.01 | 0.47 | 0.52 |
| B | 0.94 | 0.01 | 0.05 |
| C | 0.98 | 0.01 | 0.01 |
| D | 0.39 | 0.60 | 0.01 |
| E | 0.01 | 0.60 | 0.39 | where x, y and z are the mole fractions of silicon, aluminum and phosphorus and ACBDE are points defining a pentagonal area of a ternary diagram as shown in FIG. 1 of U.S. Pat. No. 4,440,871.

SUMMARY OF THE INVENTION

This invention provides a catalyst containing silicon, aluminum, phosphorus, as needed to form a silicate, aluminosilicate, aluminophosphate (AlPO) or silicoaluminophosphate (SAPO) with at least one other element selected from Group 4, Group 5, Group 13, Group 14, Group 15 and the first series transition metals in a three dimensional interconnecting crystalline tetrahedral framework. The crystalline tetrahedral framework is synthesized from an aqueous gel containing, as needed, a silica source, an aluminum source, a phosphorus source, a source for the Group 4, Group 5, Group 13, Group 14, Group 15 and the first series transition metal element(s) and, optionally, an organic structure-directing agent. The reaction mixture is heated to form crystals and then cooled. The crystals are separated from the synthesis liquor and are washed, dried and calcined. At least one metal selected from Group 6, Group 7, Group 8, Group 9 or Group 10 is deposited on the silicate, aluminosilicate, aluminophosphate or silicoaluminophosphate (hereinafter referred to as "deposited metal"). The catalyst may be used in a process for converting $C_2$-$C_{12}$ hydrocarbons into aromatics.

One example of the invention is a catalyst of a germanium zeolite on which platinum and at least one other metal selected from Group 7, Group 8, Group 9 or Group 10, such as rhenium, ruthenium, rhodium, iridium, palladium, cobalt and iron. The zeolite may be MFI (ZSM-5). This example of the invention includes a process for synthesizing the germanium zeolite catalyst by: a) preparing a germanium zeolite; b) depositing platinum and at least other metal selected from Group 7, Group 8, Group 9 or Group 10 on the germanium zeolite; and c) calcining the germanium zeolite on which platinum and the other metal has been deposited. This example of the invention also includes a process for the conversion of hydrocarbons of: a) contacting a hydrocarbon stream containing alkanes and/or olefins having 2 to 12 carbon atoms per molecule with at least one germanium zeolite catalyst comprising platinum and at least one other metal selected from Group 7, Group 8, Group 9 or Group 10 deposited on the germanium zeolite; and b) recovering the product.

BRIEF DESCRIPTION OF THE DRAWINGS

A more complete appreciation of the invention and many of the attendant advantages thereof will be readily understood by reference to the following detailed description when considered in connection with the accompanying drawings wherein.

DETAILED DESCRIPTION OF THE INVENTION

Figure 1:
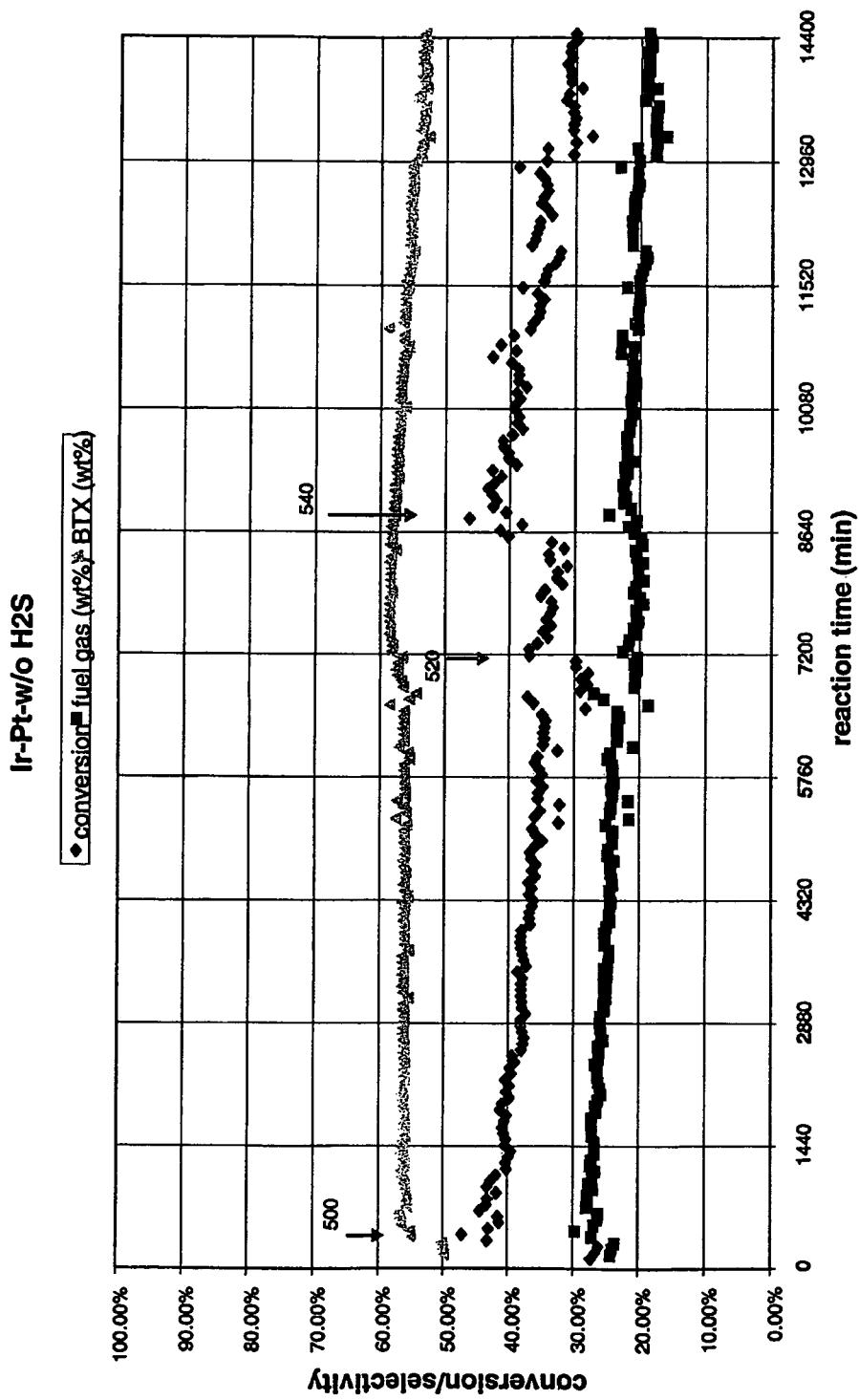
FIG. 1 is a graph of propane conversion, BTX selectivity and fuel gas selectivity for Ir—Pt/Ge-ZSM-5 without $H_2S$ pretreatment
Figure 2:
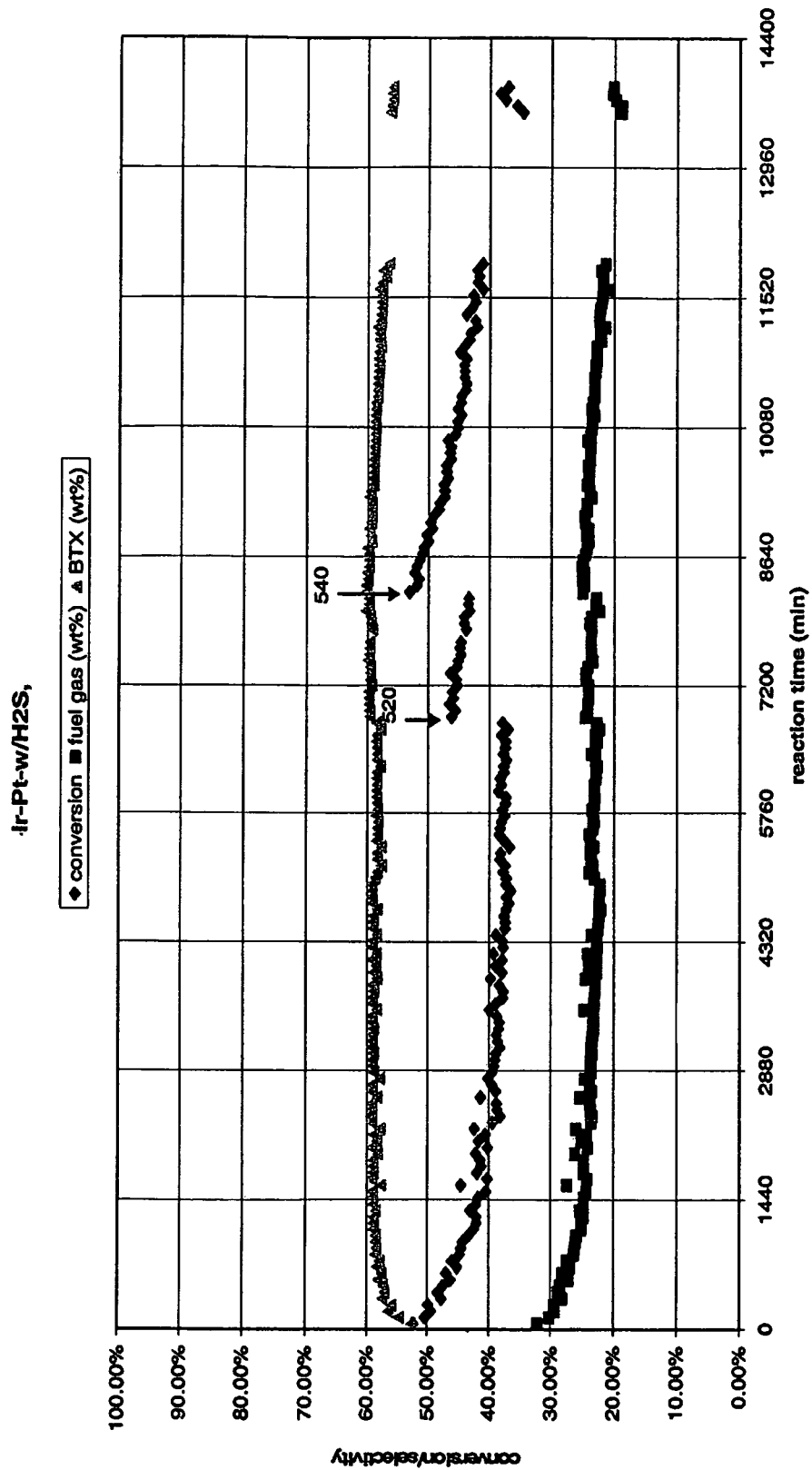
FIG. 2 is a graph of propane conversion, BTX selectivity and fuel gas selectivity for Ir—Pt/Ge-ZSM-5 with $H_2S$ pretreatment
Figure 3:
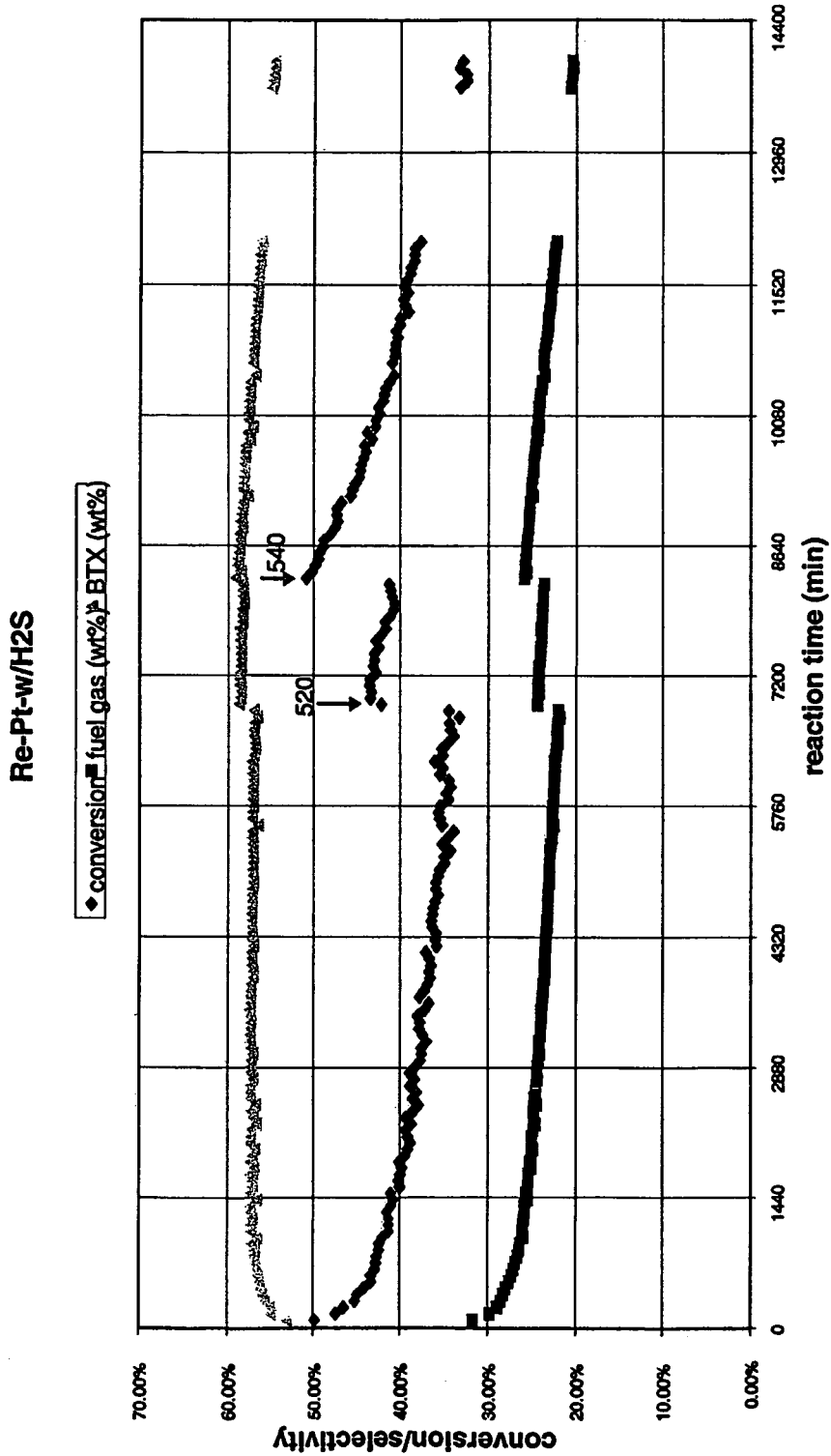
FIG. 3 is a graph of propane conversion, BTX selectivity and fuel gas selectivity for Re—Pt/Ge-ZSM-5 without $H_2S$ pretreatment
Figure 4:
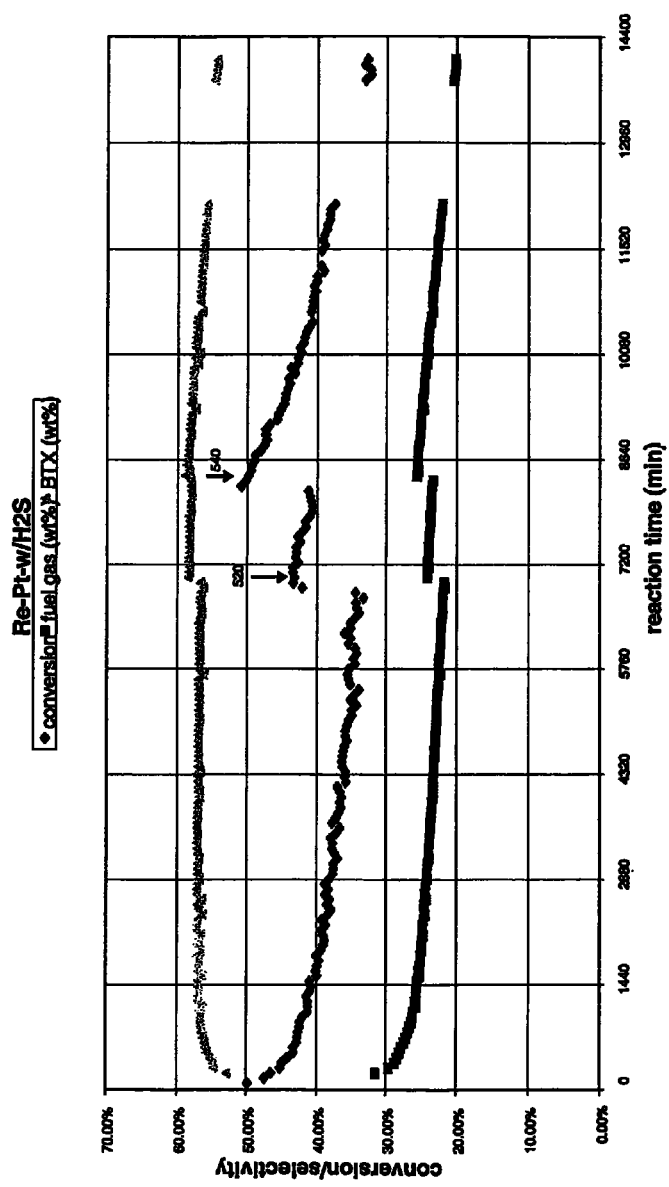
FIG. 4 is a graph of propane conversion, BTX selectivity and fuel gas selectivity for Re—Pt/Ge-ZSM-5 with $H_2S$ pretreatment
Figure 5:
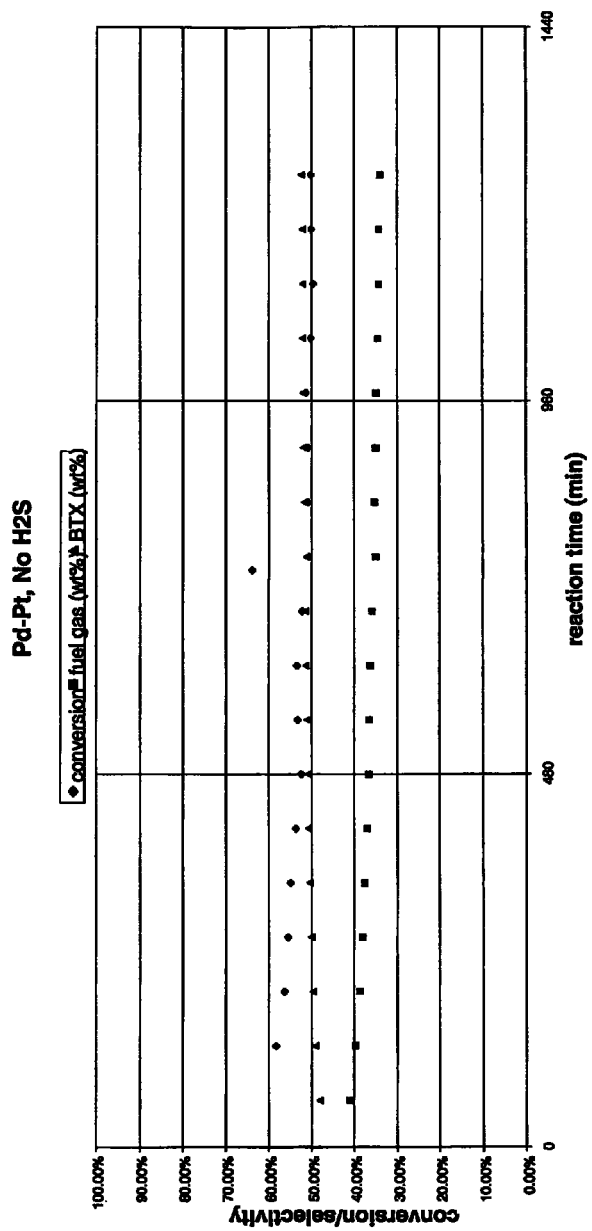
FIG. 5 is a graph of propane conversion, BTX selectivity and fuel gas selectivity for Pd—Pt/Ge-ZSM-5 without $H_2S$ pretreatment
Figure 6:
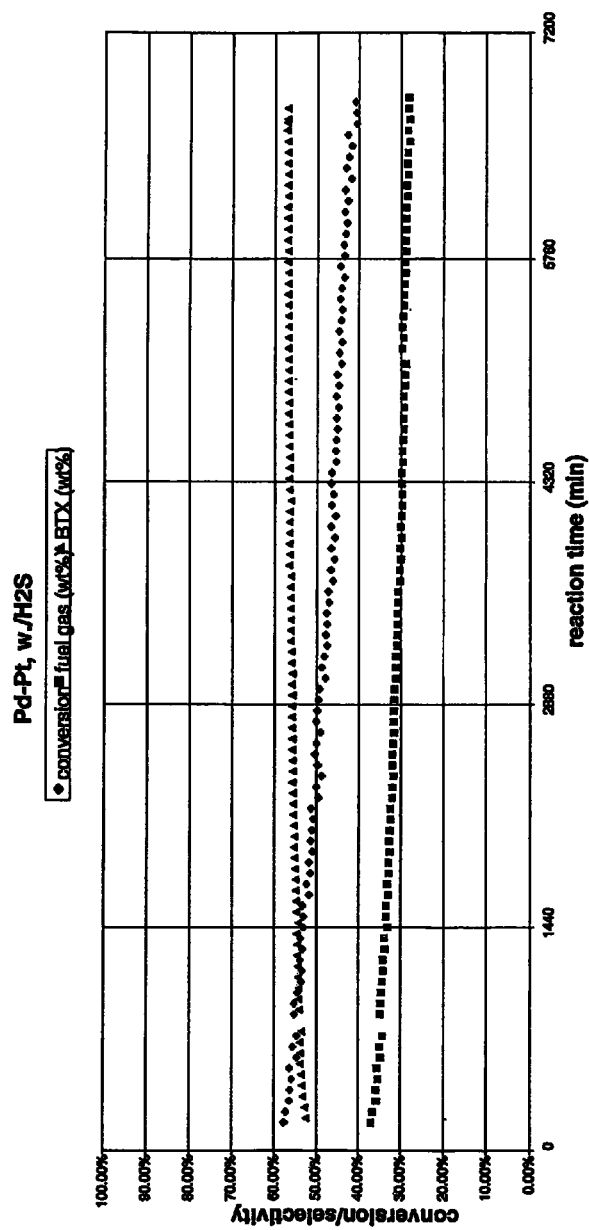
FIG. 6 is a graph of propane conversion, BTX selectivity and fuel gas selectivity for Pd—Pt/Ge-ZSM-5 with $H_2S$ pretreatment
Figure 7:
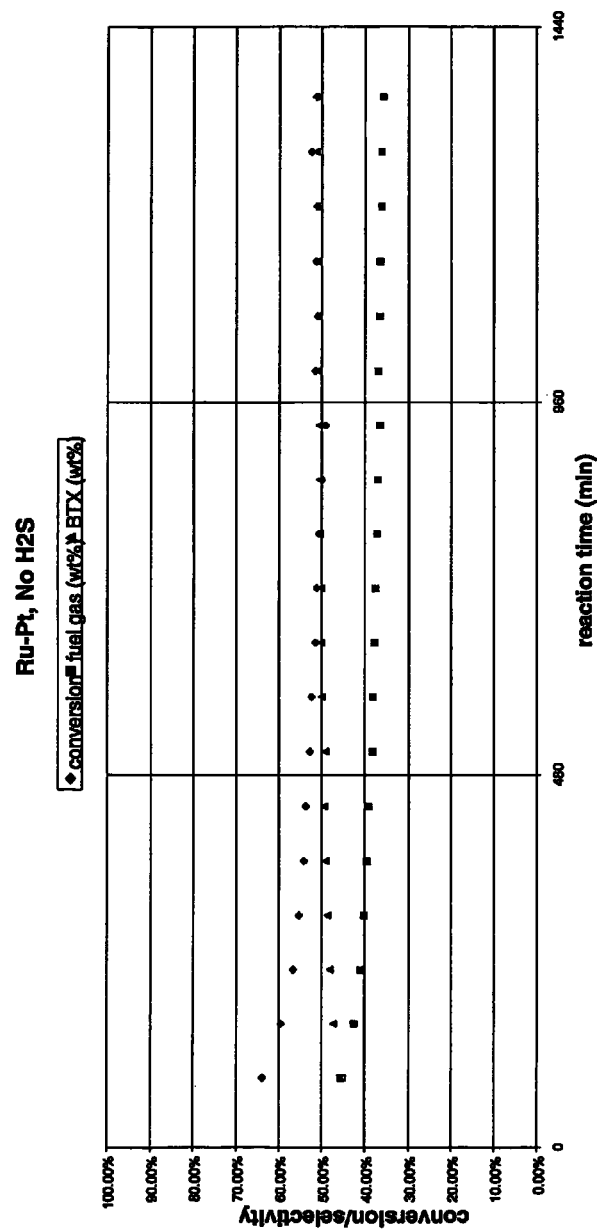
FIG. 7 is a graph of propane conversion, BTX selectivity and fuel gas selectivity for Ru—Pt/Ge-ZSM-5 without $H_2S$ pretreatment
Figure 8:
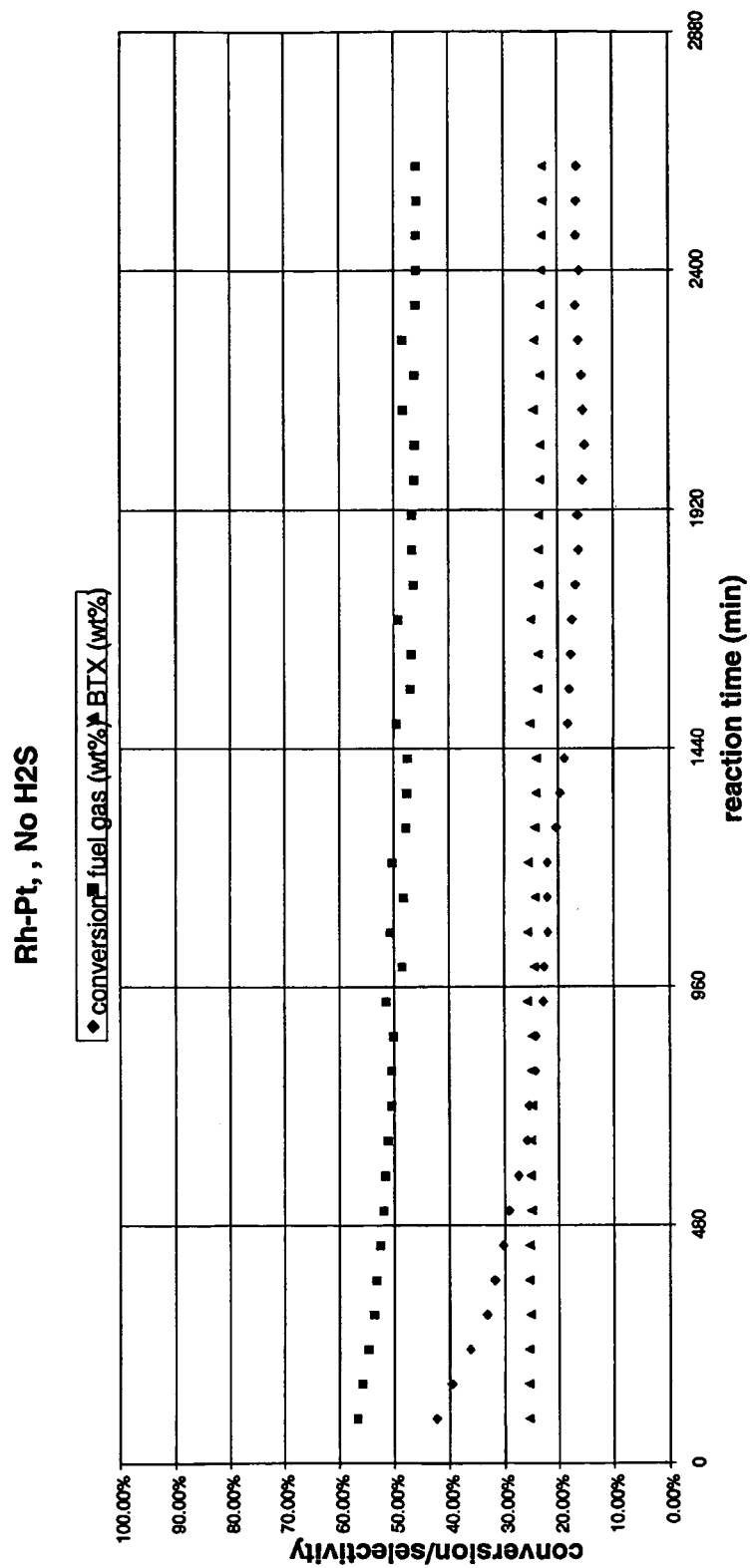
FIG. 8 is a graph of propane conversion, BTX selectivity and fuel gas selectivity for Rh—Pt/Ge-ZSM-5 without $H_2S$ pretreatment
Figure 9:
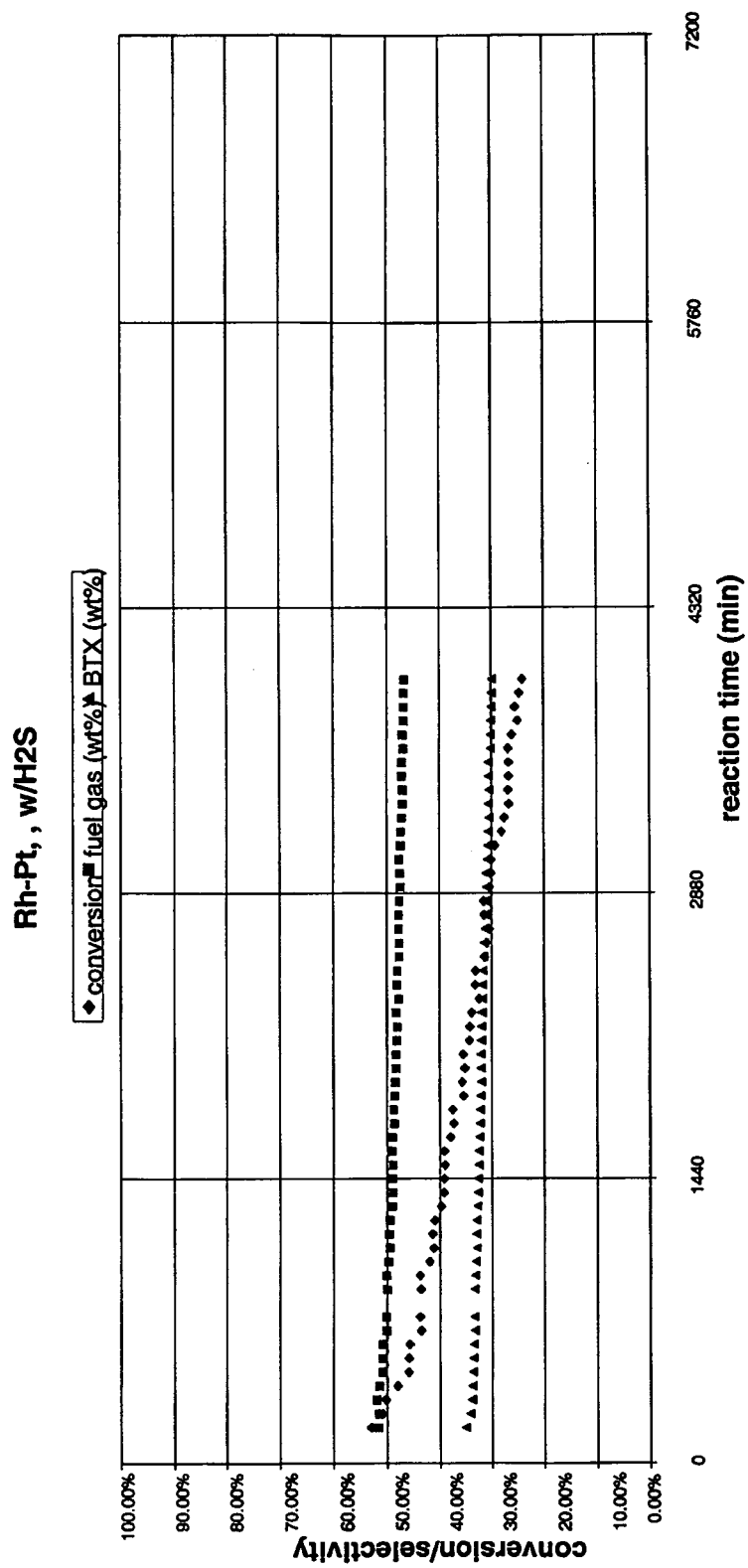
FIG. 9 is a graph of propane conversion, BTX selectivity and fuel gas selectivity for Rh—Pt/Ge-ZSM-5 with $H_2S$ pretreatment
Figure 10:
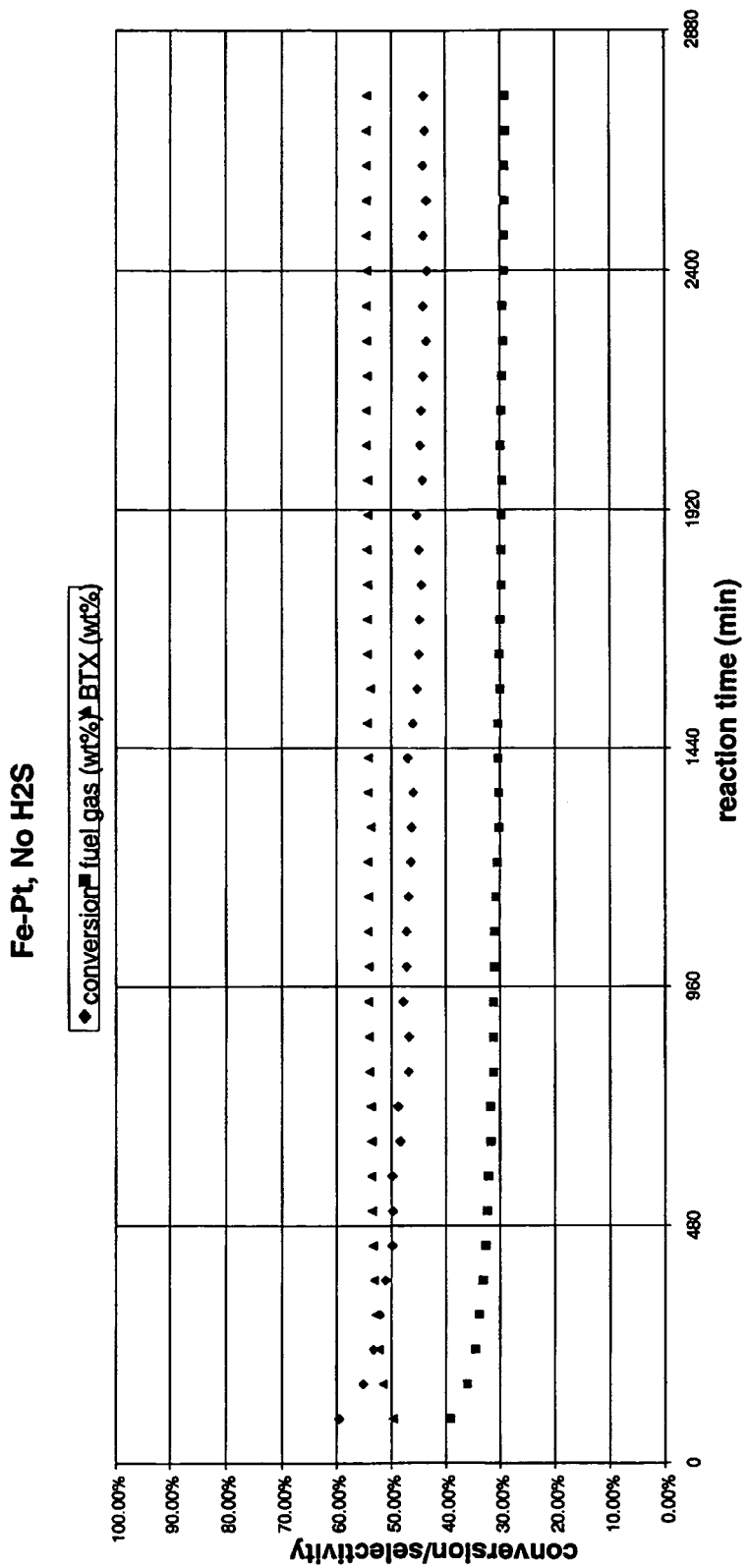
FIG. 10 is a graph of propane conversion, BTX selectivity and fuel gas selectivity for Fe—Pt/Ge-ZSM-5 without $H_2S$ pretreatment
Figure 11:
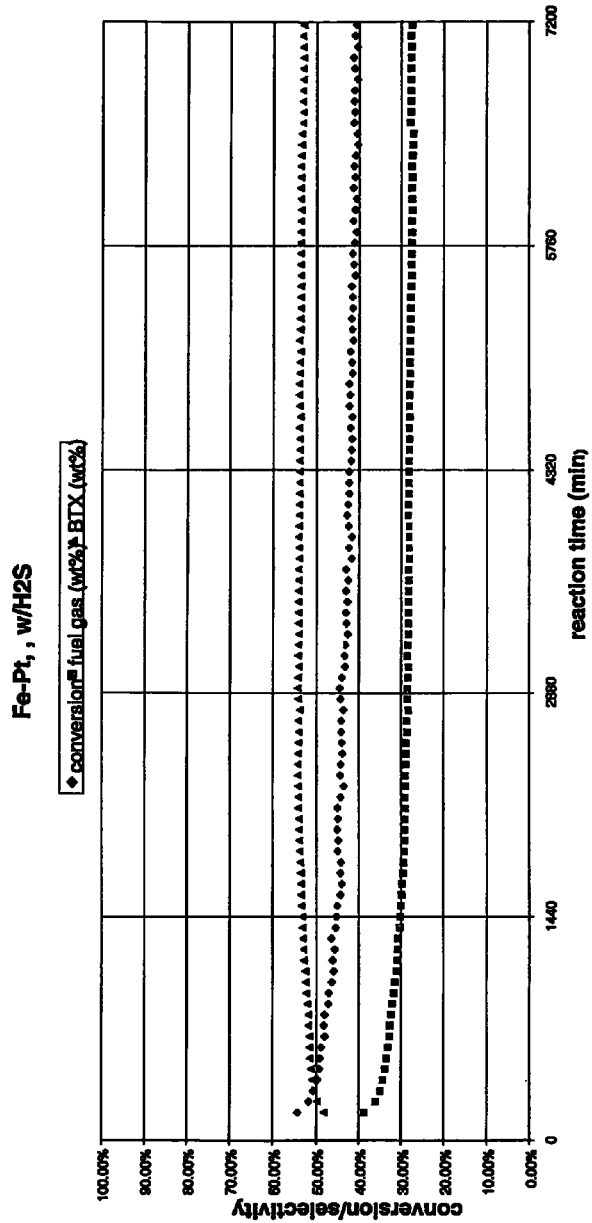
FIG. 11 is a graph of propane conversion, BTX selectivity and fuel gas selectivity for Fe—Pt/Ge-ZSM-5 with $H_2S$ pretreatment
Figure 12:
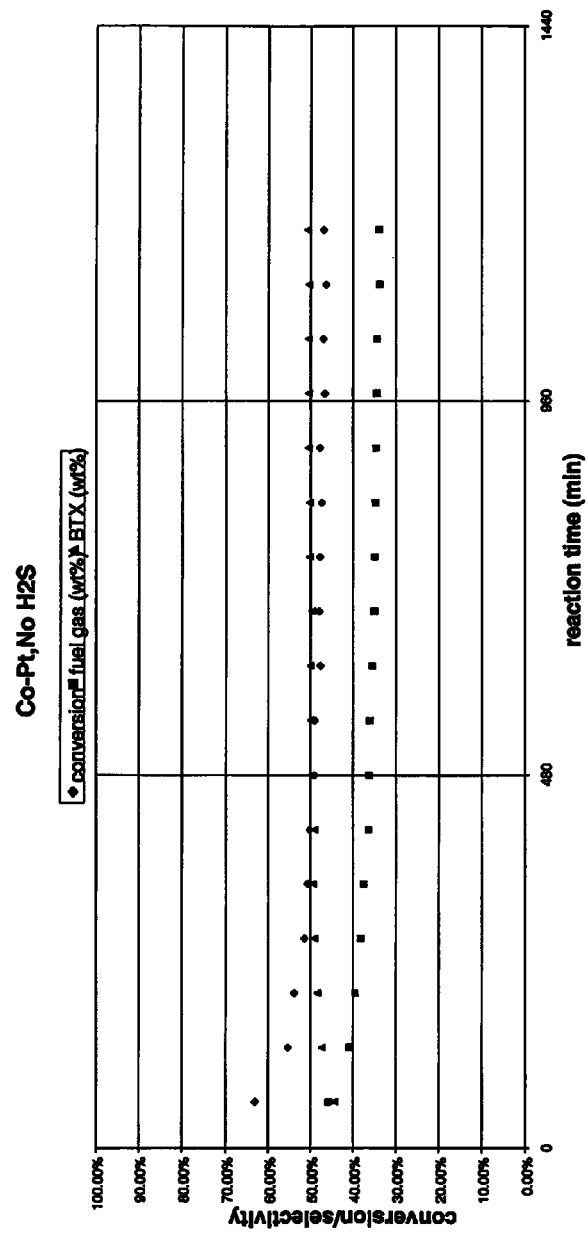
FIG. 12 is a graph of propane conversion, BTX selectivity and fuel gas selectivity for Co—Pt/Ge-ZSM-5 (Synthesis B) without $H_2S$ pretreatment
Figure 13:
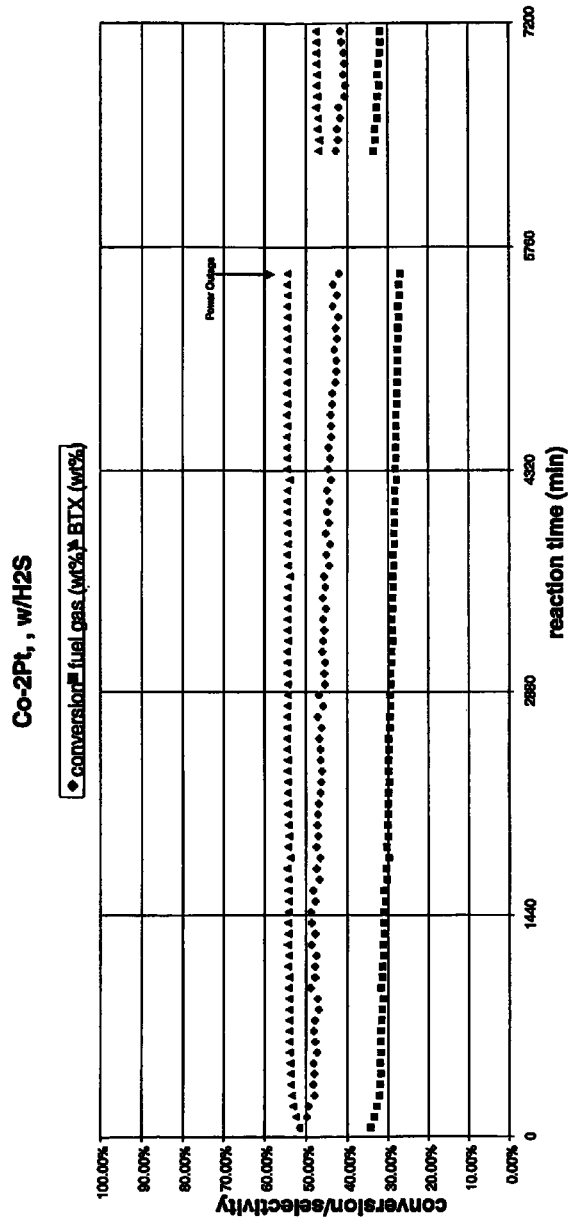
FIG. 13 is a graph of propane conversion, BTX selectivity and fuel gas selectivity for Co—Pt/Ge-ZSM-5 (Synthesis A) with $H_2S$ pretreatment
Figure 14:
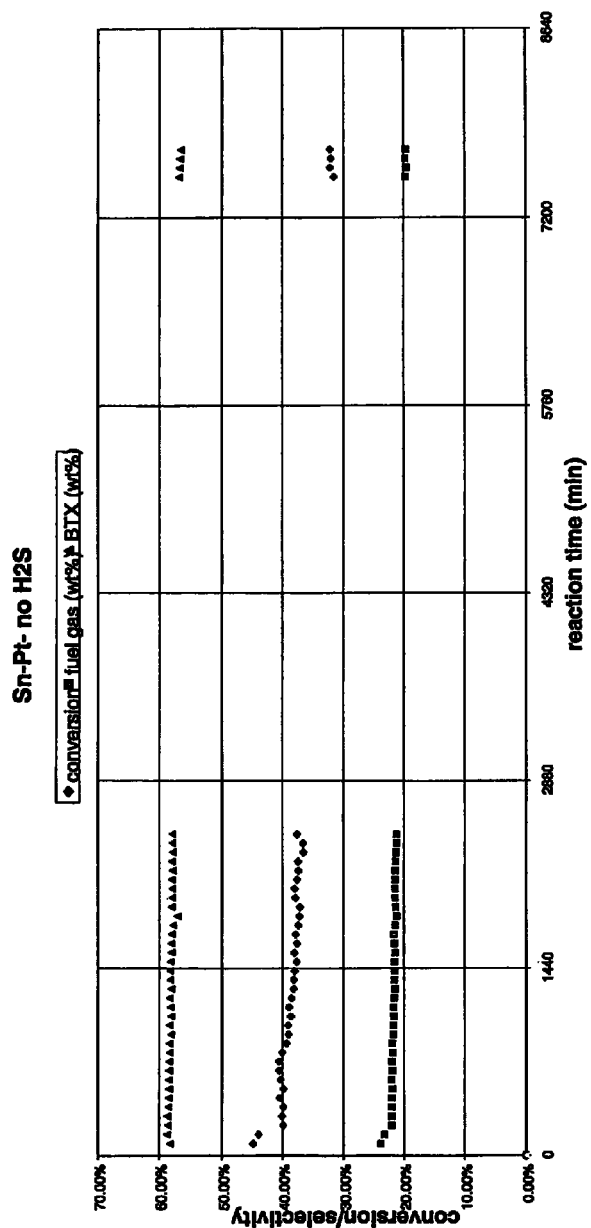
FIG. 14 is a graph of propane conversion, BTX selectivity and fuel gas selectivity for Sn—Pt/Ge-ZSM-5 without $H_2S$ pretreatment

Crystalline silicates, aluminosilicates, aluminophosphates and silicoaluminophosphates have uniform pores through which molecules can diffuse. Aluminosilicates include zeolites. Examples of zeolites are MFI (ZSM-5), BEA (Beta), MWW (MCM-22), MOR (Mordenite), LTL (Zeolite L), MTT (ZSM-23), MTW (ZSM-12), TON (ZSM-22) and MEL (ZSM-11).

Crystalline silicates, aluminosilicates, aluminophosphates and silicoaluminophosphates have structures of $TO_4$ tetrahedra, which form a three dimensional network by sharing oxygen atoms where T represents tetravalent elements, such as silicon, trivalent elements, such as aluminum, and pentavalent elements, such as phosphorus. "Zeolite" in the present application includes aluminosilicates with open three-dimensional framework structures composed of corner-sharing $TO_4$ tetrahedra, where T is Al or Si, but also includes tetravalent, trivalent and divalent T atoms which able to isoelectronically replace Si and Al in the framework, e.g., germanium (4+), titanium (4+), boron (3+), gallium (3+), iron (3+), zinc (2+) and beryllium (2+). "Zeolite" is primarily a description of structure, not composition.

Silicates, aluminosilicates, aluminophosphates and silicoaluminophosphates generally crystallize from an aqueous solution. The typical technique for synthesizing silicates, aluminosilicates, aluminophosphates or silicoaluminophosphates comprises converting an aqueous gel of a silica source, an aluminum source and a phosphorus source, as needed, to crystals by a hydrothermal process, employing a dissolution/recrystallization mechanism. The reaction medium may also contain an organic structure-directing agent which is incorporated in the microporous space of the crystalline network during crystallization, thus controlling the construction of the network and assisting to stabilize the structure through the interactions with the silicon, aluminum or phosphorus components.

The aqueous gel contains in addition to the silica source, the aluminum source, the phosphorus source, as needed, and the optional organic structure-directing agent and a source of at least one other element from Group 4, Group 5, Group 13, Group 14, Group 15 or the first series transition metals to be incorporated into the framework of the silicate, aluminosilicate, aluminophosphate or silicoaluminophosphate.

Examples of the silica source are silicon oxide or silica ($SiO_2$) which is available in various forms, such as silica sol, commercially available as Ludox AS-40™, precipitated silica, commercially available as Ultrasil VN3SP™ and fumed silica, commercially available as Aerosil 200™.

Examples of the aluminum source are sodium aluminate, aluminum nitrate, aluminum sulfate, aluminum hydroxide and pseudobohemite.

Examples of the phosphorus source are phosphoric acid (85 wt %), $P_2O_5$, orthophosphoric acid, triethylphosphate and sodium metaphosphate.

Examples of the source of Group 4, Group 5, Group 13, Group 14, Group 15 and the first series transition metals are oxides, chlorides, sulfates, alkoxides, fluorides, nitrates and oxalates.

Examples of the structure-directing agent are organic amine and quaternary ammonium compounds and salts and cations thereof, such as tetra n-propyl ammonium hydroxide, tetra n-propyl ammonium bromide and tetra n-propyl ammonium chloride, tetraethyl ammonium hydroxide, hexamethyleneimine, 1,4-di(1'4'-diazabicyclo[2.2.2]octane)butane hydroxide, morpholine, cyclohexylamine and diethylethanolamine, N,N'-diisopropyl imidazolium cation, tetrabutylammonium compounds, di-n-propylamine (DPA), tripropylamine, triethylamine (TEA), triethanolamine, piperidine, 2-methylpyridine, N,N-dimethylbenzylamine, N,N-diethylethanolamine, dicyclohexylamine, N,N-dimethylethanolamine, choline cation, N,N'-dimethylpiperazine, 1,4-diazabicyclo(2,2,2)octane, N',N',N,N-tetramethyl-(1,6) hexanediamine, N-methyldiethanolamine, N-methylethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, 2-imidazolidone, a N-benzyl-1,4-diazabicyclo [2.2.2]octane cation, a 1-[1-(4-chlorophenyl)-cyclopropylmethyl]-1-ethyl-pyrrolidinium or 1-ethyl-1-(1-phenyl-cyclopropylmethyl)-pyrrolidium cation and mixtures thereof.

The reaction may also utilize an acid as a reagent. The acid may be a Bronsted acid or a Lewis acid. Examples without limitation of an acid useful in the present invention are sulfuric acid, acetic acid, nitric acid, phosphoric acid, hydrochloric acid, hydrofluoric acid, oxalic acid or formic acid.

The reaction mixture is stirred and heated to a temperature of about 100° C. to about 200° C. to form crystals. The reaction mixture is cooled to room temperature. The crystals are separated from the synthesis liquor. The liquid portion of the synthesis liquor may be removed by filtration, evaporation, spray drying or any other means for removing liquids, e.g., water, from the crystals. The crystals are washed with water and then dried and calcined.

The silicates are essentially aluminum-free but may contain aluminum and other impurities up to 500 ppm.

The aluminosilicates may have a silicon to aluminum atomic ratio (Si:Al) greater than 2:1. In one embodiment of the present invention, the silicon to aluminum atomic ratio is in the range from 15:1 to 200:1. In another embodiment of the present invention, the silicon to aluminum atomic ratio is in the range from 18:1 to 100:1.

The aluminophosphates may have an aluminum to phosphorus atomic ratio (Al:P) in the range from about 0.8:1 to about 1.2:1 as disclosed in U.S. Pat. No. 4,310,440, hereby incorporated by reference.

The silicoaluminophosphates may have a silicon to aluminum to phosphorus atomic represented by $(S_xAl_yP_z)O_2$ where "x", "y" and "z" represent the mole fractions of silicon, aluminum and phosphorus respectively, present as tetrahedral oxides, said mole fractions being such that they are within the pentagonal compositional area defined by points ABCD and E of a ternary diagram with values represented in the table below:

|   | Mole Fraction | | |
|---|---|---|---|
|   | x | y | z |
| A | 0.01 | 0.47 | 0.52 |
| B | 0.94 | 0.01 | 0.05 |
| C | 0.98 | 0.01 | 0.01 |
| D | 0.39 | 0.60 | 0.01 |
| E | 0.01 | 0.60 | 0.39 | as disclosed in U.S. Pat. No. 4,440,871, hereby incorporated by reference.

The amount of Group 4, Group 5, Group 13, Group 14, Group 15 and the first series transition metals present in the crystalline framework is in the range from 0.1 wt. % to 25 wt. %. In one embodiment of the present invention, this range is from 0.1 wt. % to 10 wt. %. In another embodiment of the present invention, this range is from 0.1 wt. % to 5 wt. %.

The silicate, aluminosilicate, aluminophosphate or silicoaluminophosphate has average pore size in the range from 2 angstroms to 20 angstroms, i.e., microporous.

At least one metal selected from Group 6, Group 7, Group 8, Group 9 or Group 10 is deposited on the silicate, aluminosilicate, aluminophosphate or silicoaluminophosphate ("deposited metal"). The metal is deposited not only on the surface of the silicate, aluminosilicate, aluminophosphate or silicoaluminophosphate but also in the pores and channels which occur in the silicate, aluminosilicate, aluminophosphate or silicoaluminophosphate. The metal is deposited on the silicate, aluminosilicate, aluminophosphate or silicoaluminophosphate by any known method of depositing a metal on a silicate, aluminosilicate, aluminophosphate or silicoaluminophosphate. Typical methods of depositing a metal on a silicate, aluminosilicate, aluminophosphate or silicoaluminophosphate are ion exchange and impregnation. In one embodiment of the present invention, the metal is present in the range from 0.05% to 3% by weight. In another embodiment of the present invention, the metal is present in the range from 0.1% to 2% by weight. In another embodiment of the present invention, the metal is present in the range from 0.2 to 1.5% by weight.

However, for silicate, aluminosilicate, aluminophosphate or silicoaluminophosphate-based catalysts on which metals have been deposited, the process temperatures and catalyst regeneration temperatures cause the metal to "sinter", i.e., agglomeration of the metal particles resulting in an increase of metal particle size on the surface of the zeolite and a decrease of metal surface area, causing a loss of catalyst performance, specifically catalyst performance, e.g., activity and/or selectivity.

Without the present invention and its claims being limited by theory, it is believed that certain elements in the framework and certain metals deposited on the silicate, aluminosilicate, aluminophosphate or silicoaluminophosphate associate to resist sintering of the deposited metal. U.S. Pat. No. 6,784,333 discloses and claims an aluminum-silicon-germanium zeolite on which platinum has been deposited for use in a process for the aromatization of hydrocarbons. The presence of germanium in the framework of the zeolite and the presence of platinum deposited on the zeolite apparently results in higher selectivity for benzene, toluene and xylenes (BTX) which remains essentially constant over a significant time on stream. Without the invention of U.S. Pat. No. 6,784,333 and its claims being limited by theory, it may be that the germanium in the framework and the platinum deposited on the zeolite associate such that the platinum remains dispersed and sintering is reduced.

Besides germanium, there may be other elements in the crystalline framework which associate with platinum or other deposited metals. Elements in the crystalline framework may be selected from Group 4, Group 5, Group 13, Group 14, Group 15 and the first series transition metals of the Periodic Table of Elements. Specific examples of these elements are germanium, boron, gallium, indium, tin, titanium, zirconium, vanadium, chromium, iron, niobium and phosphorus. One or more elements may be in the crystalline framework.

Besides platinum, there may be other deposited metals which associate with germanium or other elements in the crystalline framework. Deposited metals may be selected from Group 6, Group 7, Group 8, Group 9 or Group 10 of the Periodic Table of Elements. Specific examples of the deposited metal are platinum, molybdenum, rhenium, nickel, ruthenium, rhodium, palladium, osmium and iridium. One or more metals, such as bimetallics, e.g., Pt/Sn, Pt/Ge, Pt/Pb or metal/metal oxide combinations, e.g. $Pt/GeO_2$, may be deposited. Specific examples of more than one metal being deposited are platinum and another metal selected from rhenium, ruthenium, rhodium, iridium or palladium.

The crystalline framework of which these elements from Group 4, Group 5, Group 13, Group 14, Group 15 and the first series transition metals are part and on which metals selected from Group 6, Group 7, Group 8, Group 9 or Group 10 are deposited need not be limited to a zeolite but may be any microporous silicate, aluminosilicate, aluminophosphate or silicoaluminophosphate.

Before or after deposition of the metal, the silicate, aluminosilicate, aluminophosphate or silicoaluminophosphate may be bound by oxides or phosphates of magnesium, aluminum, titanium, zirconium, thorium, silicon, boron or mixtures thereof. The process steps of binding and depositing metal can occur in any order. Binding may occur before or after metal deposition.

The catalyst may be calcined at different stages in the synthesis. The silicate, aluminosilicate, aluminophosphate or silicoaluminophosphate may be calcined to remove the organic structure-directing agent. This calcination is at a temperature of about 300° C. to about 1000° C. or about 300° C. to about 750° C. for a time sufficient to remove essentially all of any structure-directing agent, e.g., one to six hours or about four hours. One example of calcination is at 550° C. for ten hours. Calcination may occur after binding. This calcination is at a temperature in the range of from about 300° C. to about 1000° C. for a time in the range of from about one hour to about 24 hours. Calcination may also occur after metal deposition to fix the metal. This calcination should not exceed a temperature of 500° C. and may be at a temperature of about 200° C. to about 500° C. for a time in the range of from about 0.5 hour to about 24 hours. These calcinations need not be separate but may be combined to accomplish more than one purpose. When the silicate, aluminosilicate, aluminophosphate or silicoaluminophosphate is calcined, it may be bound or unbound and it may have metal deposited on it or not. Calcination can occur in an environment of oxygen, nitrogen, water vapor, helium and mixtures thereof.

The catalyst, bound or unbound, will have porosity in addition to the uniform porosity of the silicate, aluminosilicate, aluminophosphate or silicoaluminophosphate. For an unbound catalyst, the average pore size of the catalyst may vary in the range from 2 angstroms to 100 angstroms. In one embodiment of the present invention, the average pore size is in the range from 5 angstroms to 50 angstroms. In another embodiment of the present invention, the average pore size is in the microporous range from 5 angstroms to 20 angstroms. For a bound catalyst, the average pore size of the catalyst may vary from 5 angstroms up to 100 microns.

Some catalysts used for hydrocarbon conversion are susceptible to sulfur poisoning. However, for some catalysts used for hydrocarbon conversion, modest amounts of sulfur, such as about 0 to 200 ppm in the feed, are acceptable and sometimes preferred. The catalyst may also be pretreated with sulfur. A standard sulfurization method that is well known in the art consists in heating in the presence of a sulfur compound, such as hydrogen sulfide, or a mixture of a sulfur compound and an inert gas, such as hydrogen or nitrogen, to a temperature of between 150 and 800° C. Non-limiting examples of sulfur compounds are $H_2S$, an organosulfide compound, such as dimethyl disulfide or DMSO (dimethyl sulfoxide), or $C_nH_{2n+2}S$ or $C_nH_{2n+2}S_2$, where n=1-20. In one embodiment of the present invention, the temperature is between 250 and 600° C.

The catalyst may contain a reaction product, such as a sulfide of the deposited metal, that is formed by contacting the catalyst with sulfur or a sulfur compound. In one embodiment of the present invention, the amount of sulfur on the catalyst is in the range of from 10 ppm to 0.1 wt. %.

The catalyst may also contain elements other than sulfur, such as tin, germanium or lead. These elements would be present in the range of from 1:1 to 1:100 as a ratio of the deposited metal to tin, germanium or lead. These elements may be added to the catalyst by wet impregnation, chemical vapor deposition or other methods known in the art.

The silicate, aluminosilicate, aluminophosphate or silicoaluminophosphate-based catalyst which contains at least one element selected from Group 4, Group 5, Group 13, Group 14, Group 15 and the first series transition metals isomorphously incorporated into the zeolite framework and at least one metal selected from Group 6, Group 7, Group 8, Group 9 or Group 10 deposited on the zeolite can be used in a process for conversion of hydrocarbon streams containing $C_2$-$C_{12}$ alkanes, olefins and mixtures thereof, said alkanes and olefins which may be straight, branched, cyclic or mixtures thereof, into aromatics.

The zeolite may be base-exchanged with an alkali metal or alkaline earth metal, such as cesium, potassium, sodium, rubidium, barium, calcium, magnesium and mixtures thereof, to reduce acidity and form a non-acidic zeolite. A non-acidic zeolite has substantially all of its cationic sites of exchange, e.g., those typically associated with aluminum, occupied by nonhydrogen cationic species, e.g., alkali or alkaline earth metals. The base-exchange may occur before or after the noble metal is deposited. Such a base-exchanged catalyst may be used to convert $C_6$-$C_{12}$ alkanes, olefins and mixtures thereof, such as might be obtained from natural gas condensate, light naphtha, raffinate from aromatics extraction and other refinery or chemical processes, to aromatics, such as benzene, ethyl benzene, toluene and xylenes. Base-exchange may take place during synthesis of the zeolite with an alkali metal or alkaline earth metal being added as a component of the reaction mixture or may take place with a crystalline zeolite before or after deposition of the noble metal. The zeolite is base-exchanged to the extent that most or all of the cations associated with aluminum are alkali metal or alkaline earth metal. An example of a monovalent base:aluminum molar ratio in the zeolite after base exchange is at least about 0.9. For a divalent or trivalent base, the molar ratio would be half (0.45) or a third (0.3) as that for a monovalent base, respectively, and for mixtures of monovalent, divalent and trivalent bases, the above molar ratios would be apportioned by their respective content in the mixture.

Depending on the element incorporated into the zeolite framework, the zeolite may be non-acidic within the present invention without base-exchange, e.g., boron, germanium or tin in an aluminum-free zeolite. "Aluminum-free" has a meaning of having aluminum content of no more than 0.4 wt %. Within the meaning and for the purposes of the present invention, a zeolite may be non-acidic by exchange with a base or by having a low aluminum content.

Examples of hydrocarbon conversion processes for which this catalyst can be used are:

(A) The catalytic cracking of a naphtha feed to produce light olefins. Typical reaction conditions include from about 500° C. to about 750° C., pressures of subatmospheric or atmospheric, generally ranging up to about 10 atmospheres (gauge) and catalyst residence time (volume of the catalyst/feed rate) from about 10 milliseconds to about 10 seconds.

(B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 to about 100 $hr^{-1}$.

(C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 to about 100 $hr^1$ and an aromatic hydrocarbon/polyalkylaromatic hydrocarbon mole ratio of from about 1/1 to about 16/1.

(D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 to about 200 $hr^{-1}$ and a hydrogen/hydrocarbon mole ratio of from about 0 to about 100.

(E) The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 3,000 psig and a liquid hourly space velocity from 0.1 to 20 $hr^{-1}$.

(F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 $hr^{-1}$ to about 100 $hr^{-1}$ and an aromatic hydrocarbon/alkylating agent mole ratio of from about 1/11 to about 20/1.

(G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1. The resulting products from the reaction are long chain alkyl aromatics which when subsequently sulfonated have particular application as synthetic detergents.

(H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 $hr^{-1}$ to about 50 $hr^{-1}$.

(I) The hydrocracking of heavy petroleum feedstocks, cyclic stocks, and other hydrocrack charge stocks. The zeolite-bound high silica zeolite will contain an effective amount of at least one hydrogenation component of the type employed in hydrocracking catalysts.

(J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 to about 800 psig, a WHSV-olefin from about 0.4 hr$^{-1}$ to about 0.8 hr$^{-1}$, a WHSV-reformate of from about 1 hr$^{-1}$ to about 2 hr$^{-1}$ and, optionally, a gas recycle from about 1.5 to 2.5 vol/vol fuel gas feed.

(K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 100° C. to about 400° C. and pressures from about 50 to 450 psig.

(L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 hr$^{-1}$ to about 10 hr$^{-1}$.

(M) The conversion of light paraffins to olefins and/or aromatics. Typical reaction conditions include temperatures from about 425° C. to about 760° C. and pressures from about 10 to about 2000 psig.

(N) The conversion of light olefins to gasoline, distillate and lube range hydrocarbons. Typical reaction conditions include temperatures of from about 175° C. to about 500° C. and a pressure of from about 10 to about 2000 psig.

(O) Two-stage hydrocracking for upgrading hydrocarbon streams having initial boiling points above about 200° C. to premium distillate and gasoline boiling range products or as feed to further fuels or chemicals processing steps. The first stage can be the zeolite-bound high silica zeolite comprising one or more catalytically active substances, e.g., a Group 8 metal, and the effluent from the first stage would be reacted in a second stage using a second zeolite, e.g., zeolite Beta, comprising one or more catalytically active substances, e.g., a Group 8 metal, as the catalyst. Typical reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10 hr$^{-1}$.

(P) A combination hydrocracking/dewaxing process in the presence of the zeolite-bound high silica zeolite comprising a hydrogenation component and a zeolite such as zeolite Beta. Typical reaction conditions include temperatures from about 350° C. to about 400° C., pressures from about 1400 to about 1500 psig, LHSV from about 0.4 to about 0.6 hr$^{-1}$ and a hydrogen circulation from about 3000 to about 5000 SCF/bbl.

(Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram of olefin per hour per gram of zeolite) from about 0.1 hr$^{-1}$ to about 200 hr$^{-1}$ and an alcohol to olefin molar feed ratio from about 0.1/1 to about 5/1.

(R) The disproportionation of aromatics, e.g. the disproportionation of toluene to make benzene and xylenes. Typical reaction conditions include a temperature of from about 200° C. to about 760° C., a pressure of from about atmospheric to about 60 atmosphere (bar), and a WHSV of from about 0.1 hr$^{-1}$ to about 30 hr$^{-1}$.

(S) The conversion of naphtha (e.g., $C_6$-$C_{10}$) and similar mixtures to highly aromatic mixtures. Thus, normal and slightly branched chained hydrocarbons, preferably having a boiling range above about 40° C., and less than about 200° C., can be converted to products having a substantially higher octane aromatics content by contacting the hydrocarbon feed with the zeolite at a temperature in the range of from about 400° C. to 600° C., preferably 480° C. to 550° C. at pressures ranging from atmospheric to 40 bar, and liquid hourly space velocities (LHSV) ranging from 0.1 to 15 hr$^{-1}$.

(T) The adsorption of alkyl aromatic compounds for the purpose of separating various isomers of the compounds.

(U) The conversion of oxygenates, e.g., alcohols, such as methanol, or ethers, such as dimethylether, or mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100.

(V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous phase with a zeolite-bound high silica zeolite at a temperature in the range of from about 250° C. to about 800° C., a LHSV of from about 0.2 to about 50 and a hydrocarbon partial pressure of from about 0.1 to about 50 atmospheres. Temperatures below about 250° C. may be used to oligomerize the feedstock when the feedstock is in the liquid phase when contacting the zeolite-bound high silica zeolite catalyst. Thus, when the olefin feedstock contacts the catalyst in the liquid phase, temperatures of from about 10° C. to about 250° C. can be used.

(W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

(X) The desulfurization of FCC (fluid catalytic cracking) feed streams. The desulfurization process is generally carried out at a temperature ranging from 100° C. to about 600° C., preferably from about 200° C. to about 500° C., and more preferably from about 260° C. to about 400° C., at a pressure ranging from 0 to about 2000 psig, preferably from about 60 to about 1000 psig, and more preferably from about 60 to about 500 psig, at a LHSV ranging from 1 to 10 h$^{-1}$. The hydrocarbon mixtures which can be desulfurized according to the process of the present invention contain more than 150 ppm of sulfur, e.g., hydrocarbon mixtures with a sulfur content higher than 1000 ppm, even higher than 10000 ppm.

The invention having been generally described, the following examples are given as particular embodiments of the invention and to demonstrate the practice and advantages thereof. It is understood that the examples are given by way of illustration and are not intended to limit the specification or the claims to follow in any manner.

Synthesis of Ge-ZSM-5

Chemicals Used:

"Ludox AS-40 colloidal silica $SiO_2$; 40 wt. % suspension in water; Aldrich;

Sodium hydroxide NaOH, 50 wt. % solution in water; Sigma-Aldrich;

Germanium dioxide $GeO_2$; Germanium Corporation of America GTAH 68002;

Sodium aluminate $NaAlO_2$ (23.6 wt. % $Al_2O_3$; 19.4 wt. % $Na_2O$; 57.0 wt. % $H_2O$); Southern Ionics;

Tetrapropylammonium hydroxide $(CH_3CH_2CH_2)_4NOH$, 40 wt. % solution in water; SACHEM;

Acetic acid $CH_3CO_2H$, 99.7%; Aldrich.

Solution 1.

18.1 grams of sodium hydroxide solution was mixed with 155 grams of D.I. water. 7.4314 grams of $GeO_2$ were dissolved in the solution with stiffing.

Solution 2.

1.93 grams of sodium aluminate were mixed with 165 grams of D.I. water.

Solution 1 was poured into 160 grams of Ludox AS-40 with vigorous gel stirring for 40 minutes. Solution 2 was introduced into gel with stirring for 10 minutes. Tetrapropylammonium hydroxide (112.46 grams) was added to the mixture and gel was stirred for about one hour.

25.73 grams of acetic acid was added to gel with continuous stirring. pH of gel in ten minutes was 9.10.

Crystallization was made in 1 L stainless steel autoclave at 160° C. with stirring (300 rpm) for 36 hours. Zeolite was filtered and washed with D.I. water. Zeolite was dried at 90° C. overnight and was calcined at 550° C. for 10 hours in an oven with forced air flow.

Example 1

Synthesis of Pt—Ir/Ge-ZSM-5

Chemicals Used:

Ammonium hexachloroiridate(III) hydrate $(NH_4)_2IrCl_6.H_2O$; (% Ir 38.9%); Strem Chemicals;

Tetraammineplatinum (II) nitrate $(NH_2)_4Pt(NO_3)_2$; Aldrich;

Ethylenediaminetetraacetic acid $(HO_2CCH_2)_2NCH_2CH_2N(CH_2CO_2H)_2$; 99%; Alfa-Aesar;

Ammonium hydroxide $NH_4OH$, 28-30%; Alfa-Aesar.

Ge-ZSM-5 zeolite powder as prepared above was used for catalyst preparation.

0.525 gram of ethylenediaminetetraacetic acid in 8 grams of D.I. water were heated up and 1 ml of ammonium hydroxide was added to dissolve the acid. 0.184 gram of ammonium hexachloroiridate(III) hydrate was dissolved in this solution with stirring. After solution was cooled down 19 ml of water was added. pH of solution was 9.70.

Solution was impregnated into 10 grams of Ge-ZSM-5 powder. Paste was dried at 60° C. overnight with following calcination at 550° C. for 10 hours.

Calcined powder was bound with silica at 50/50 wt. Material was calcined at 550° C. for 6 hours. Sample was crushed and sized to 20/40 mesh.

Platinum was introduced by incipient wetness impregnation technique. Solution of tetraammineplatinum (II) nitrate in water was impregnated into the sample by portions in 3 steps with intermediate drying at 90° C. Catalyst was calcined at 300° C. for 5 hours.

XRF analysis results are: 0.12% Na; 43.61% Si; 0.37% Al; 2.81% Ge; 0.26%; Ir; 0.36% Pt.

Example 2

Synthesis of Pt—Re/Ge-ZSM-5

Chemicals Used:

Ammonium perrhenate $NH_4ReO_4$; 99+%; Aldrich Chemicals;

Tetraammineplatinum (II) nitrate $(NH_2)_4Pt(NO_3)_2$; Aldrich;

Ethylenediaminetetraacetic acid $(HO_2CCH_2)_2NCH_2CH_2N(CH_2CO_2H)_2$; 99%; Alfa-Aesar;

Ammonium hydroxide $NH_4OH$, 28-30%; Alfa-Aesar.

Ge-ZSM-5 zeolite powder as prepared above was used for catalyst preparation.

0.525 grams of ethylenediaminetetraacetic acid in 8 grams of D.I. water were heated up and 1 ml of ammonium hydroxide was added to dissolve the acid. 0.100 gram of ammonium perrhenate was dissolved in this solution with stirring. After solution was cooled down 19 ml of water was added. pH of solution was 9.50. Solution was impregnated into 10 grams of Ge-ZSM-5 powder. Paste was dried at 60° C. overnight with following calcination at 600° C. for 10 hours.

Calcined powder was bound with silica at 50/50 wt. Material was calcined at 550° C. for 6 hours. Sample was crushed and sized to 20/40 mesh.

Platinum was introduced by incipient wetness impregnation technique. Solution of tetraammineplatinum (II) nitrate in water was impregnated into the sample by portions in 3 steps with intermediate drying at 90° C. Catalyst was calcined at 300° C. for 5 hours.

XRF analysis results are: 0.12% Na; 43.76% Si; 0.37% Al; 2.84% Ge; 0.11%; Re; 0.37% Pt.

Example 3

Synthesis of Pt—Pd/Ge-ZSM-5

Chemicals Used:

Palladium nitrate $Pd(NO_3)_2$; 99.999%; 10 wt. % in 10 wt. % nitric acid; Aldrich;

Tetraammineplatinum (II) nitrate $(NH_2)_4Pt(NO_3)_2$; Aldrich.

Ge-ZSM-5 powder was bound with silica at 50/50 wt. Material was calcined at 550° C. for 6 hours. Sample was sized to 20/40 mesh. Bound zeolite was ammonium ion-exchanged with 0.5M $NH_4NO_3$ solution at 60° C. three times.

Sample was calcined at 550° C. for 6 hours. Sample was ion-exchanged with 0.002M $Pd(NO_3)_2$ solution at 60° C. in four steps in four days. Sample was washed several times with D.I. water, dried at 90° C. and calcined at 300° C. for 5 hours.

Platinum was introduced into sample by ion-exchange procedure. Ion-exchange was made at 60° C. by using 0.005M $(NH_2)_4Pt(NO_3)_2$ solution.

XRF analysis results are: 0.00% Na; 43.91% Si; 0.36% Al; 1.86% Ge; 0.22% Pd; 0.37% Pt.

Example 4

Synthesis of Pt—Ru/Ge-ZSM-5

Chemicals Used:

Ammonium aquopentachlororuthenate (III) $(NH_4)_2[RuCl_5(H_2O)]$; Alfa-Aesar;

Tetraammineplatinum (II) nitrate $(NH_2)_4Pt(NO_3)_2$; Aldrich.

Ge-ZSM-5 powder was bound with silica at 50/50 wt. Material was calcined at 550° C. for 6 hours. Sample was sized to 20/40 mesh.

Bound zeolite was ammonium ion-exchanged with 0.5M $NH_4NO_3$ solution at 60° C. three times. Sample was calcined at 550° C. for 6 hours.

Sample was ion-exchanged with 0.002M $(NH_4)_2[RuCl_5(H_2O)]$ solution at 80° C. for 17 hours. Sample was washed several times with D.I. water, dried at 60° C. and calcined at 300° C. for 5 hours.

Platinum was introduced into sample by ion-exchange procedure. Ion-exchange was made at 60° C. by using 0.005M $(NH_2)_4Pt(NO_3)_2$ solution.

XRF analysis results are: 0.01% Na; 43.58% Si; 0.36% Al; 2.11% Ge; 0.24% Ru; 0.34% Pt.

Example 5

Synthesis of Pt—Rh/Ge-ZSM-5

Chemicals Used:

Rhodium (III) chloride hydrate $RhCl_3 \cdot xH_2O$; 38-40% Rh; Aldrich; Tetraammineplatinum (II) nitrate $(NH_2)_4Pt(NO_3)_2$; Aldrich.

Ge-ZSM-5 powder was bound with silica at 50/50 wt. Material was calcined at 550° C. for 6 hours. Sample was sized to 20/40 mesh.

Bound zeolite was ammonium ion-exchanged with 0.5M $NH_4NO_3$ solution at 60° C. three times. Sample was calcined at 550° C. for 6 hours.

Sample was ion-exchanged with 0.002M $RhCl_3 \cdot xH_2O$ solution at 80° C. in four steps in four days. Sample was washed several times with D.I. water, dried at 90° C. and calcined at 300° C. for 5 hours.

Platinum was introduced into sample by ion-exchange procedure. Ion-exchange was made at 60° C. by using 0.005M $(NH_2)_4Pt(NO_3)_2$ solution.

XRF analysis results are: 0.00% Na; 43.61% Si; 0.36% Al; 1.82% Ge; 0.13% Rh; 0.35% Pt.

Example 6

Synthesis of Pt—Fe/Ge-ZSM-5

Chemicals Used:

Iron acetate $Fe(MCO_2)_2$; 99.995%; Aldrich;

Tetraammineplatinum (II) nitrate $(NH_2)_4Pt(NO_3)_2$; Aldrich.

Ge-ZSM-5 powder was bound with silica at 50/50 wt. Material was calcined at 550° C. for 6 hours. Sample was sized to 20/40 mesh.

Bound zeolite was ammonium ion-exchanged with 0.5M $NH_4NO_3$ solution at 60° C. three times. Sample was calcined at 550° C. for 6 hours.

Sample was ion-exchanged with 0.028M $Fe(MCO_2)_2$ solution at RT with stirring for about 18 hours. Sample was washed several times with D.I. water, dried at 60° C. and calcined at 300° C. for 5 hours.

Platinum was introduced into sample by ion-exchange procedure. Ion-exchange was made at 60° C. by using 0.005M $(NH_2)_4Pt(NO_3)_2$ solution.

XRF analysis results are: 0.05% Na; 43.67% Si; 0.38% Al; 2.31% Ge; 0.47% Fe; 0.36% Pt.

Example 7

Syntheses of Pt—Co/Ge-ZSM-5

Synthesis A and Synthesis B

Chemicals Used:

Cobalt acetate $Co(MCO_2)_2$; 99.995%; Aldrich;

Tetraammineplatinum (II) nitrate $(NH_2)_4Pt(NO_3)_2$; Aldrich.

Ge-ZSM-5 powder was bound with silica at 50/50 wt. Material was calcined at 550° C. for 6 hours. Sample was sized to 20/40 mesh.

Bound zeolite was ammonium ion-exchanged with 0.5M $NH_4NO_3$ solution at 60° C. three times. Sample was calcined at 550° C. for 6 hours.

Sample was ion-exchanged with 0.09M $Co(MCO_2)_2$ solution at 60° C. in two steps, each for about 3-5 hours. Sample was washed several times with D.I. water, dried at 60° C. and calcined at 300° C. for 5 hours.

Platinum was introduced into sample by ion-exchange procedure. Ion-exchange was made at 60° C. by using 0.005M $(NH_2)_4Pt(NO_3)_2$ solution.

XRF analysis results for Synthesis A: 0.03% Na; 43.93% Si; 0.37% Al; 2.13% Ge; 0.31% Co; 0.41% Pt.

XRF analysis results for Synthesis B: 0.00% Na; 44.07% Si; 0.39% Al; 2.13% Ge; 0.62% Co; 0.36% Pt.

Example 8

Pt—Sn/Ge-ZSM-5

Chemicals Used:

Tin (II) chloride dihydrate $SnCl_2 \cdot 2H_2O$; 98%; Aldrich Chemicals;

Tetraammineplatinum (II) nitrate $(NH_2)_4Pt(NO_3)_2$; Aldrich;

Ethylenediaminetetraacetic acid $(HO_2CCH_2)_2NCH_2CH_2N(CH_2CO_2H)_2$; 99%; Alfa-Aesar;

Ammonium hydroxide $NH_4OH$, 28-30%; Alfa-Aesar.

Ge-ZSM-5 zeolite powder was used for catalyst preparation. 1.254 grams of ethylenediaminetetraacetic acid in 2 grams of D.I. water were heated up and 1 ml of ammonium hydroxide was added to dissolve the acid. 0.0855 gram of tin chloride dehydrate was dissolved in this solution with stirring. After solution was cooled down 19 ml of water was added. pH of solution was 6.59. Solution was impregnated into 10 grams of Ge-ZSM-5 powder. Paste was dried at 60° C. overnight with following calcination at 550° C. for 10 hours.

Calcined powder was bound with silica at 50/50 wt. Material was calcined at 550° C. for 6 hours. Sample was crushed and sized to 20/40 mesh.

Platinum was introduced by incipient wetness impregnation technique. Solution of tetraammineplatinum (II) nitrate in water was impregnated into the sample by portions in 3 steps with intermediate drying at 90° C. Catalyst was calcined at 300° C. for 5 hours.

XRF analysis results are: 0.13% Na; 43.48% Si; 0.36% Al; 2.84% Ge; 0.22%; Sn; 0.36% Pt.

All catalysts were reduced in a flowing hydrogen/nitrogen (50/50 by volume) mixture at 400° C. Some catalysts as indicated were pretreated with 1 vol % hydrogen sulfide in a nitrogen gas stream until sulfide breakthrough achieved and then swept with hydrogen/nitrogen (50/50 by volume) at 400° C. for approximately one hour to remove excess sulfur. All catalysts were tested in a stainless steel tube at 500° C. using 34 cc/min of propane at 22 psig total pressure. The products were analyzed by on-line sampling to a gas chromatograph where all hydrocarbon components with carbon numbers between 1 and 10 were quantitatively determined. Results for yield [fraction of BTX (benzene, toluene, xylenes) in product] and conversion (portion of propane converted) are shown in the graphs below.

Numerous modifications and variations of the present invention are possible in light of the above teachings. It is to be understood that, within the scope of the appended claims, the invention may be practiced other than as specifically described.

What is claimed as new and desired to be secured by letter of patent of the United States of America is:

1. A catalyst for conversion of hydrocarbons comprising:
   a) a germanium zeolite; and
   b) platinum and a metal selected from Group 7, Group 8, Group 9, and Group 10, deposited on the germanium zeolite.

2. The catalyst of claim 1 wherein the metal is rhenium, ruthenium, rhodium, iridium, palladium, cobalt, and/or iron.

3. The catalyst of claim 1 wherein the zeolite is MFI.

4. The catalyst of claim 2 wherein the other metal is rhenium, rhodium, iridium, and/or palladium.

5. The catalyst of claim 3 wherein the zeolite is ZSM-5.

6. A process for synthesizing a germanium zeolite catalyst comprising:
   a) preparing a germanium zeolite;
   b) depositing platinum and a metal selected from Group 7, Group 8, Group 9, Group 10 or tin on the germanium zeolite; and
   c) calcining the germanium zeolite, said calcining occurring after preparation of the zeolite, before depositing platinum and the metal on the germanium zeolite or before or after depositing platinum and the metal on the germanium zeolite.

7. The process of claim 6 wherein the metal is rhenium, ruthenium, rhodium, iridium, palladium, cobalt, and/or iron.

8. The process of claim 6 wherein the zeolite is MFI.

9. The process of claim 8 wherein the zeolite is ZSM-5.

10. A process for the conversion of hydrocarbons comprising:
    a) contacting a hydrocarbon stream containing alkanes, olefins or mixtures thereof having 2 to 12 carbon atoms per molecule with a germanium zeolite catalyst comprising platinum and a metal selected from Group 7, Group 8, Group 9 or Group 10 deposited on the germanium zeolite; and
    b) recovering the product.

11. The process of claim 10 wherein the other metal is rhenium, ruthenium, rhodium, iridium, palladium, cobalt, and/or iron.

12. The process of claim 10 wherein the zeolite is MFI.

13. The process of claim 10 wherein alkanes or olefins are straight, branched, cyclic, or mixtures thereof.

14. The process of claim 10 wherein the zeolite is ZSM-5.

* * * * *